(12) United States Patent
Goshert

(10) Patent No.: US 7,530,982 B1
(45) Date of Patent: May 12, 2009

(54) COMPOSITE ALLOGRAFT FORMATION INSTRUMENT

(75) Inventor: David Goshert, Pierceton, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 550 days.

(21) Appl. No.: 10/960,422

(22) Filed: Oct. 7, 2004

(51) Int. Cl.
| | |
|---|---|
| A61B 17/58 | (2006.01) |
| A61F 2/28 | (2006.01) |
| B28B 7/22 | (2006.01) |
| B29C 70/80 | (2006.01) |
| B29C 45/00 | (2006.01) |
| B29C 67/24 | (2006.01) |
| A61F 2/00 | (2006.01) |

(52) U.S. Cl. .................. 606/95; 606/99; 623/23.48; 623/23.63; 264/255; 264/268; 264/328.2; 264/328.7; 264/330

(58) Field of Classification Search .............. 623/17.11, 623/17.12, 17.13, 17.14, 17.15, 17.16, 23.48, 623/23.63; 606/92, 93, 94, 95, 99; 264/241, 264/250, 255, 259, 260, 266, 267, 268, 269, 264/299, 308, 319, 334, 328.1, 328.2, 328.7, 264/328.13, 330
See application file for complete search history.

(56) References Cited

U.S. PATENT DOCUMENTS

| | | | |
|---|---|---|---|
| 5,133,771 A * | 7/1992 | Duncan et al. ............. 623/23.2 |
| 5,329,846 A | 7/1994 | Bonutti |
| 5,545,222 A | 8/1996 | Bonutti |
| 5,662,710 A | 9/1997 | Bonutti |
| 5,755,720 A * | 5/1998 | Mikhail ....................... 606/94 |
| 5,888,219 A | 3/1999 | Bonutti |
| 6,132,472 A | 10/2000 | Bonutti |
| 6,216,493 B1 * | 4/2001 | Weston et al. .................. 65/68 |
| 6,280,675 B1 * | 8/2001 | Legrand ..................... 264/262 |
| 6,361,565 B1 | 3/2002 | Bonutti |
| 6,402,784 B1 * | 6/2002 | Wardlaw ................. 623/17.11 |
| 6,503,277 B2 | 1/2003 | Bonutti |
| 6,595,998 B2 * | 7/2003 | Johnson et al. ............... 606/90 |
| 6,638,309 B2 | 10/2003 | Bonutti |
| 6,702,856 B2 | 3/2004 | Bonutti |
| 6,752,809 B2 * | 6/2004 | Gorek ......................... 606/92 |
| 6,835,336 B2 * | 12/2004 | Watt ........................... 264/28 |
| 6,994,726 B2 * | 2/2006 | Lin et al. ................. 623/16.11 |
| 7,087,082 B2 * | 8/2006 | Paul et al. ................ 623/17.11 |
| 7,153,305 B2 * | 12/2006 | Johnson et al. ............... 606/90 |
| 7,166,133 B2 * | 1/2007 | Evans et al. .............. 623/23.51 |
| 2002/0040246 A1 | 4/2002 | Bonutti |
| 2003/0045934 A1 | 3/2003 | Bonutti |
| 2003/0050708 A1 | 3/2003 | Bonutti |
| 2003/0125811 A1 | 7/2003 | Bonutti |
| 2003/0130744 A1 | 7/2003 | Bonutti |
| 2005/0228498 A1 * | 10/2005 | Andres .................... 623/17.11 |

* cited by examiner

Primary Examiner—Thomas J Sweet
(74) Attorney, Agent, or Firm—Harness, Dickey

(57) ABSTRACT

A graft formation and delivery instrument comprising an outer barrel, a piston, and an inner pin. The outer barrel has a center aperture. The piston is seated within the center aperture, has a through bore, and is operable to move within the center aperture. The inner pin is seated within the through bore of the piston and operable to move within the through bore. The outer barrel receives multiple graft components that are contacted by at least one of the piston and the inner pin to assemble a composite graft from the graft components. The instrument is operable to direct the composite graft to a desired implant area and deposit the composite graft at the implant area.

36 Claims, 5 Drawing Sheets

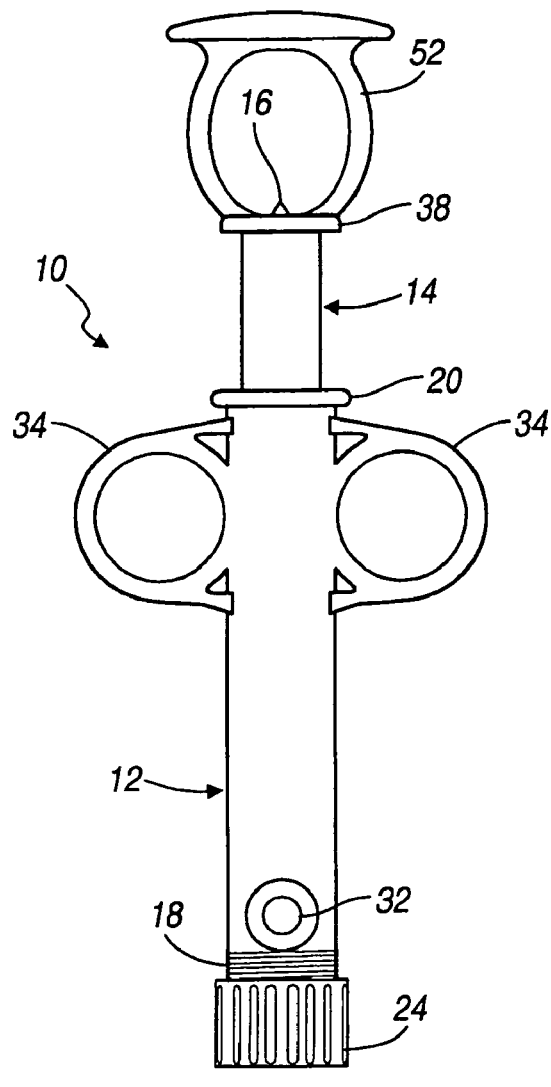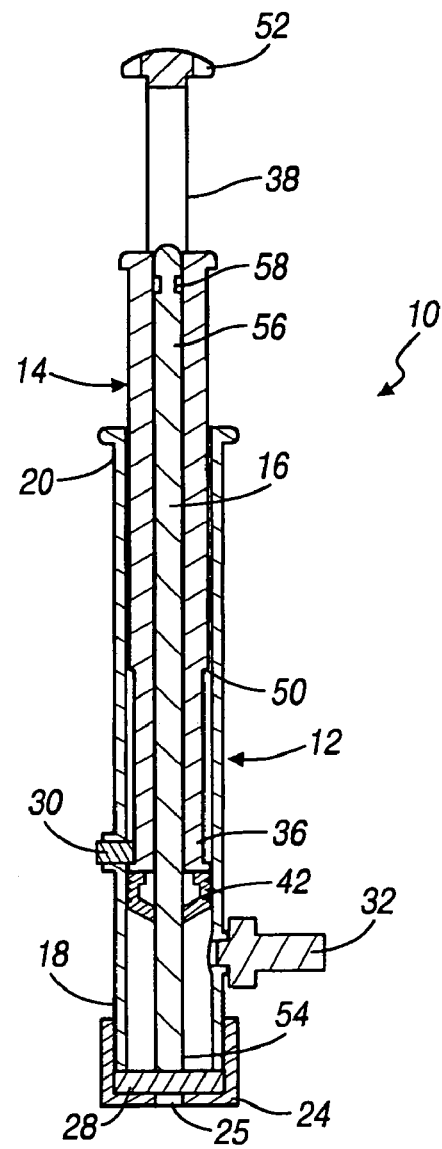
FIG. 2                    FIG. 3

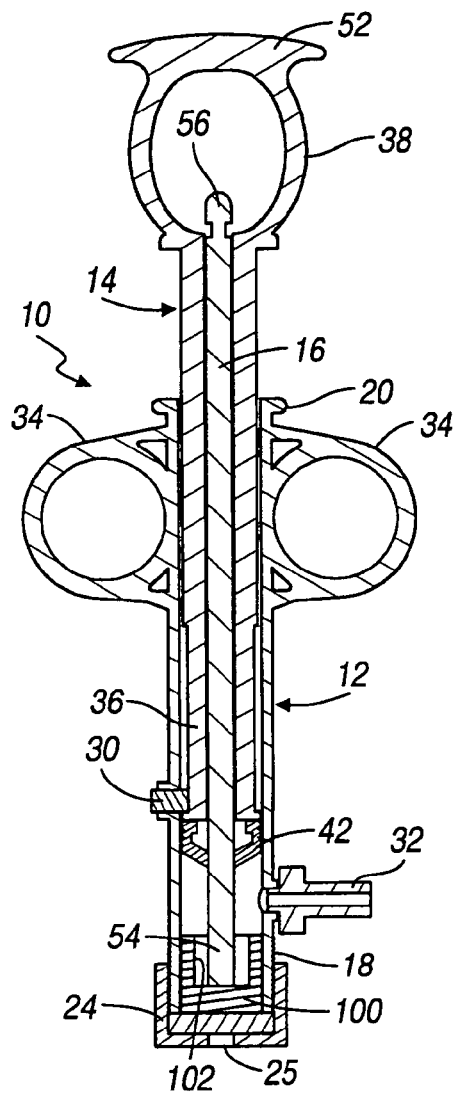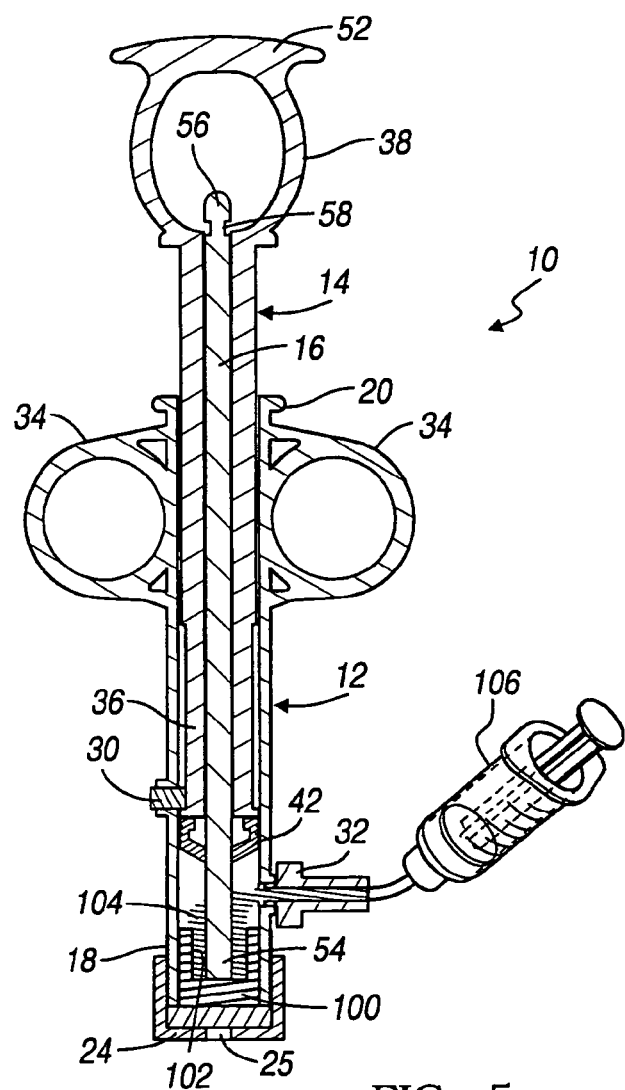
FIG. 4
FIG. 5

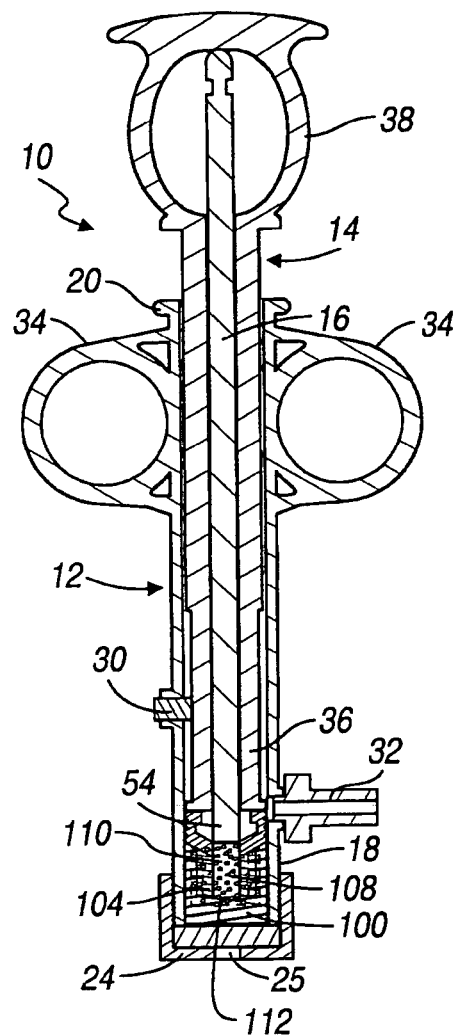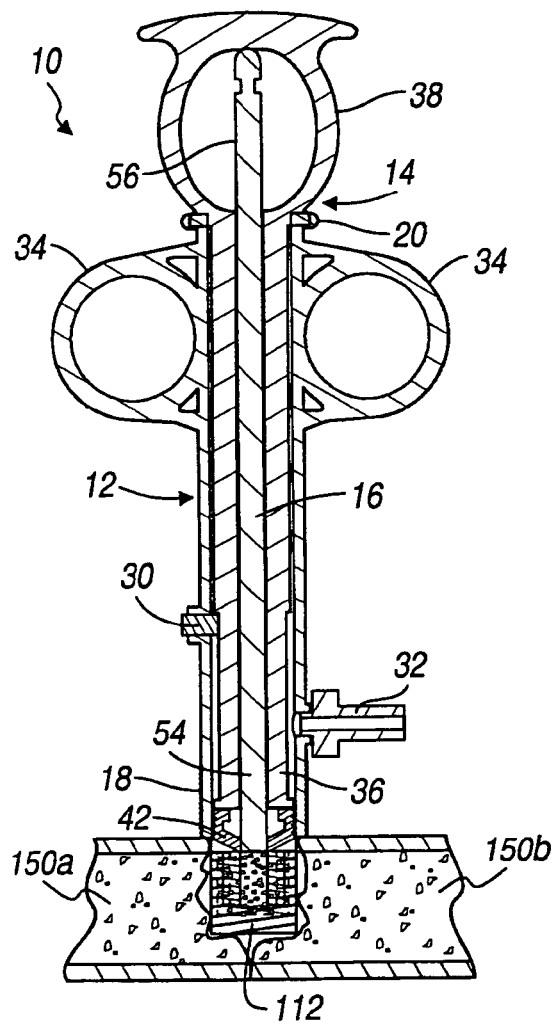
FIG. 8
FIG. 9

COMPOSITE ALLOGRAFT FORMATION INSTRUMENT

FIELD OF THE INVENTION

The present invention relates to medical devices. In particular, the present invention relates to an instrument having multiple concentric plungers for forming a composite graft.

BACKGROUND OF THE INVENTION

Composite grafts, such as allografts and autografts, are often used to treat damaged bone or tissue. Such composite grafts are conventionally assembled manually by a surgeon or other trained professional in-vivo. Manual assembly of the graft in-vivo often results in wasted graft material. Further, manual construction of the graft in-vivo may make it difficult to precisely form the different layers of the graft and to fully compress the different graft layers together.

Therefore, there is a need for an improved device that can permit assembly of a composite graft in an in-vivo environment. The device can allow the surgeon to form the composite graft and insure the fabrication of a sterile graft. Further, the device can also eliminate wasted graft material and insure that the full amount of the different graft components is incorporated into the assembled graft. Still further, the device can facilitate insertion of the graft at the implant site.

SUMMARY OF THE INVENTION

The present invention provides for a graft formation and delivery instrument comprising an outer barrel, a piston, and an inner pin. The outer barrel has a center aperture. The piston is seated within the center aperture, has a through bore, and is operable to move within the center aperture. The inner pin is seated within the through bore of the piston and operable to move within the through bore. The outer barrel receives multiple graft components that are contacted by at least one of the piston and the inner pin to assemble a composite graft from the graft components. The instrument is operable to direct the composite graft to a desired implant area and deposit the composite graft at the implant area.

The present invention further provides for an implant formation instrument comprising an outer barrel, a piston, and an inner pin. The outer barrel has a first end and a second end opposite the first end. The implant is formed proximate to the first end. The piston has a through bore and a tip. The piston is seated within the outer barrel. The inner pin is seated within the through bore of the piston. The tip of the piston and the inner pin are moved distal to the first end to accommodate a first component of the implant. The inner pin is moved proximate to the first end to at least nearly abut the implant to facilitate the insertion of a second component of the implant between the inner pin and the first component. The tip is extended toward the first end to contact and compress the second component. The inner pin is moved distal to the first end to accommodate the insertion of a third implant component. The inner pin and the piston are together moved toward the first end to compress the third component.

The present invention still further provides for a method for forming a composite graft. The method includes the steps of inserting a first graft component having a first cavity within an outer barrel of a graft formation instrument having a piston movably seated within the outer barrel and an inner pin movably seated within the piston; moving the inner pin into the cavity of the first graft component; inserting a second graft component between the first graft component and the cavity; compressing the second graft component and the first graft component together using the piston; moving the inner pin and the piston distal to the first and second graft components to expose a second cavity in the second graft component; inserting a third graft component in the second cavity; compressing the third graft component, the second graft component, and the first graft component together using both the piston and the inner pin to form the composite graft; directing the composite graft to an implantation site; and ejecting the composite graft from the instrument using the piston and the inner pin.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is an assembled side view of the instrument of FIG. 1;

FIG. 3 is a cross-sectional view of FIG. 2;

FIG. 4 is similar to FIG. 3, but further illustrates a first graft component inserted within the instrument;

FIG. 5 is similar to FIG. 4, but further illustrates a second graft component being inserted within the instrument;

FIG. 8 is a cross-sectional view of the instrument and illustrates the third graft component being compressed by both the piston and an inner pin; and FIG. 9 is a cross-sectional view of the instrument and an injured bone, the instrument being used to direct the implant to the bone and insert the implant in the bone.

DETAILED DESCRIPTION

The following description of the embodiments is merely exemplary in nature and is in no way intended to limit the invention, its application, or uses.

Figure 1:
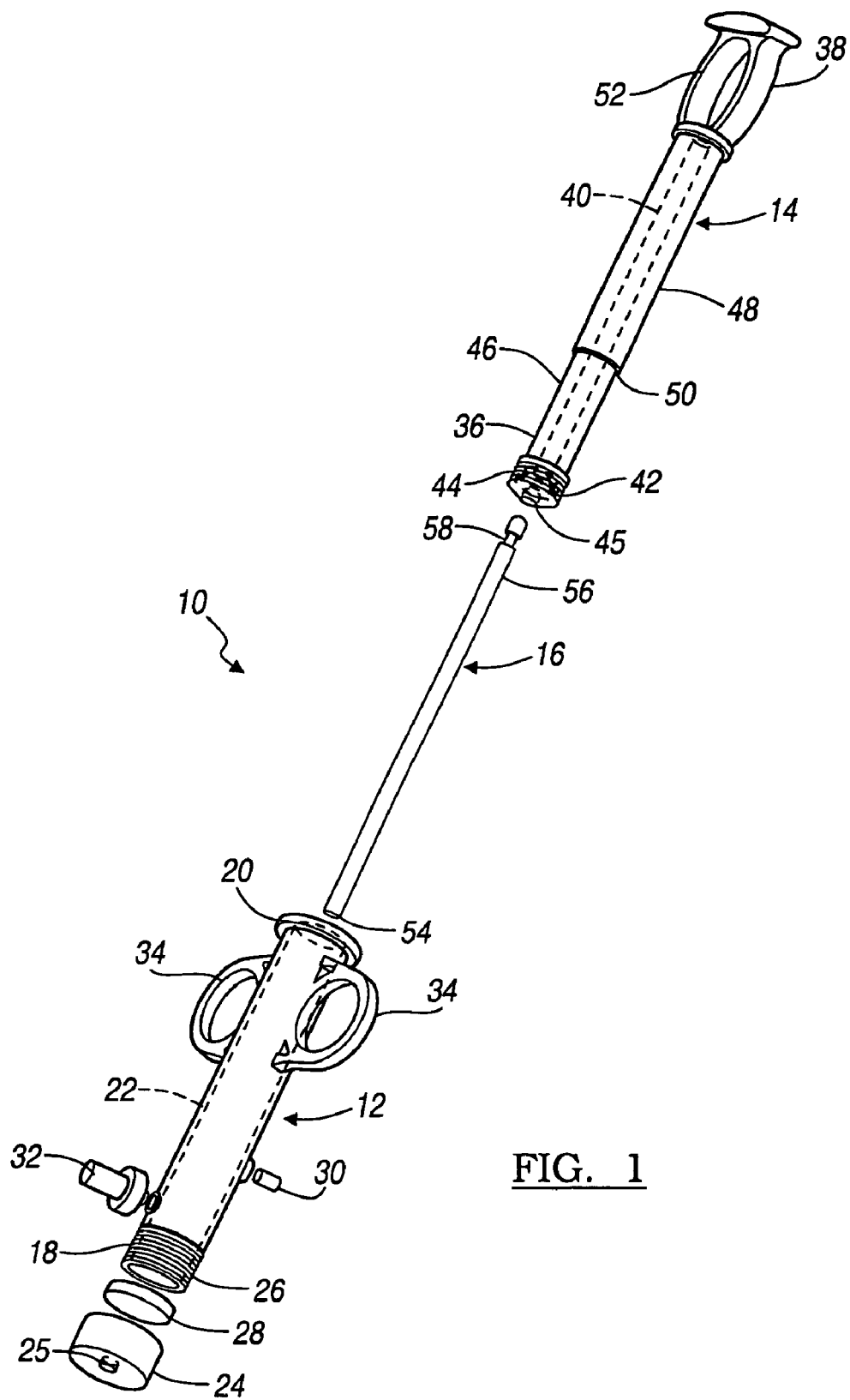
FIG. 1 is an exploded perspective view of a graft formation and delivery instrument according to a preferred embodiment of the present invention.

With initial reference to FIG. 1, a graft formation and delivery instrument according to an embodiment of the present invention is illustrated at 10. The instrument generally includes a main body or outer barrel 12, a piston 14, and an inner pin 16.

The outer barrel 12 generally includes a first end 18 and a second end 20 opposite the first end 18. Extending through the barrel 12 between the first end 18 and the second end 20 is a center aperture 22. The first end 18 is covered by an end cap 24 having an air hole 25. The first end 18 has threads 26 that cooperate with similar threads (not shown) of the end cap 24 to secure the end cap 24 to the first end 18 and close the center aperture 22 at the first end 18. A filter 28 can be positioned between the end cap 24 and the first end 18. The filter 28 allows air to pass into and out of the outer barrel 12 while at the same time preventing graft material from exiting the outer barrel 12 through the air hole 25.

Between the first end 18 and the second end 20 is a stop pin 30. The stop pin 30 extends through the outer surface of the outer barrel 12 to within the center aperture 22 (FIG. 3). Between the stop pin 30 and the first end 18 is a valve 32. The valve 32 is a one way valve that provides a port to insert materials within the center aperture 22, but prevents materials from exiting the center aperture 22 through the valve 32. The valve 32 can be any suitable one way valve, such as a luer valve.

Proximate to the second end 20 of the outer barrel 12 is a handle 34. The handle 34 can be grasped by an operating surgeon to operate the instrument 10 and to direct the instrument 10 to a desired implant site.

With continued reference to FIG. 1, the piston 14 generally includes a first end 36 and a second end 38 opposite the first end 36. Extending between the first end 36 and the second end 38 is a through bore 40. At the first end 36 is a tip 42. The tip 42 includes a plurality of fins 44 that extend horizontally from the tip 42. The fins 44 can be flexible fins. The tip 42 further includes an opening 45

Between the first end 36 and the second end 38, the piston 14 includes a first diameter portion 46 and a second diameter portion 48. The first diameter portion 46 is proximate to the first end 36 and the second diameter portion 48 is proximate to the second end 38. The first diameter portion 46 has a diameter that is smaller than the second diameter portion 48. The diameter of the tip 42 is larger than the diameter of the first diameter portion 46 and approximates the diameter of the second diameter portion 48. Where the second diameter portion 48 meets the first diameter portion 46 is a detail 50 or shoulder that is the result of the second diameter portion 48 having a diameter larger than the first diameter portion 46.

Proximate to the second end 38 of the piston 14 is a handle 52. The handle 52 can be any suitable handle that allows actuation and manipulation of the piston 14. As illustrated, the handle 52 is a single loop handle.

With further reference to FIG. 1, the inner pin 16 is an elongated pin having a first end 54 and a second end 56. The pin 16 has a diameter that is slightly smaller than an inner diameter of the through bore 40 and is thus sized to be received by the through bore 40. The second end 56 includes a notch 58. The notch 58 is a recess within the pin 16 and facilitates movement of the pin by a surgeon.

FIGS. 2 and 3 illustrate an assembled view of the instrument 10. The piston 14 is seated within the center aperture 22 of the outer barrel 12 and is able to slide vertically, in the orientation illustrated, within the center aperture 22. The piston 14 is positioned within the center aperture 22 such that the first diameter portion 46 abuts the stop pin 30 and such that the stop pin 30 is located between the tip 42 and the detail 50.

The inner pin 16 is seated within the through bore 40 of the piston 14. The inner pin 16 can move vertically within the through bore 40. More specifically, the inner pin 16 can move to the first end 36 of the piston 14 and through the opening 45 of the tip 42 (FIG. 3). Further, the inner pin 16 can move through the second end 38 of the piston 14 until it contacts the handle 52. Contact between the inner pin 16 prevents the inner pin 16 from being removed from the assembly.

Use of the instrument 10 to form a composite graft is illustrated in FIGS. 4 through 8. While the graft is described as an allograft, other composite grafts, such as an autograft, can also be formed. First, as illustrated in FIG. 4, the piston 14 is moved toward the second end 20 of the barrel 12, such as to a point where the tip 42 of the piston 14 contacts the stop pin 30. The inner pin 16 is then moved such that the first end 54 of the pin 16 extends through the opening 45 of the tip 42 and is positioned near the first end 18 of the barrel 12. After the piston 14 and the inner pin 16 are in position, the first allograft component 100 is inserted at the first end 18 of the outer barrel 12. The first component 100 can be inserted by removing the end cap 24 and the filter 28 and inserting the first component 100 at the first end 18. Further, depending on the composition of the first component 100, the first component 100 can be inserted by injecting the first component 100 through the valve 32.

Figure 6:
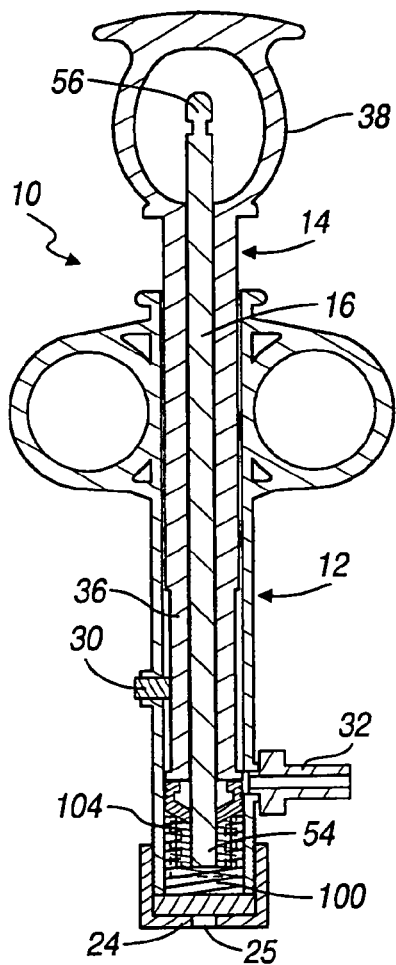
FIG. 6 is similar to FIG. 5, but illustrates the second graft component being compressed by a piston.

With reference to FIGS. 5 and 6, after the first component 100 is in position and the pin 16 is seated within the cavity 102, the second component 104 is added. The second component 104 is inserted into the center aperture 22 through the valve 32. The second component 104 can be inserted through the valve 32 using any suitable instrument, such as a syringe 106. The second component 104 is inserted within the cavity 102 such that a portion of the second component 104 is seated between the first component 100 and the inner pin 16 and a portion of the second component 104 is seated above the first component 100.

With reference to FIG. 6, after the second component 104 has been inserted within the center aperture 22, the piston 14 is moved toward the first end 18 of the outer barrel 12 so that the tip 42 of the piston 14 contacts the second component 104 to compress the second component 104 into the first component 100 and into the cavity 102. The porous nature of the first component 100 allows the first component 100 to absorb the second component 104.

Figure 7:
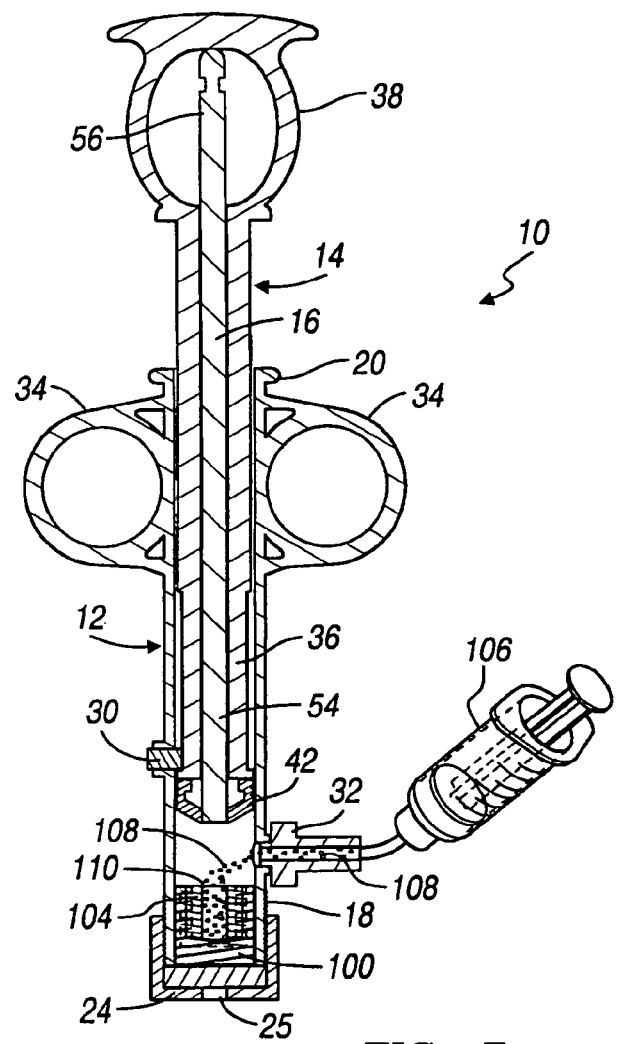
FIG. 7 is a cross-sectional view of the instrument and illustrates a third graft component being added to the instrument.

With reference to FIG. 7, after the second component 104 has been compressed into the first component 100 and into the cavity 102 of the first component 100, the inner pin 16 and the piston 14 are moved upward towards the second end 20 of the outer barrel 12 to accommodate the third component 108. Movement of the inner pin 16 from within the cavity 102 reveals a second cavity 110 that is defined by the second component 104.

The third component 108 is also delivered to the center aperture 22 through the valve 32. The third component 108 can be delivered through the valve 32 using the syringe 106 or any other suitable device or method. The third component 108 is deposited within the second cavity 110 defined by the second component 104 with a portion of the third component 108 also being deposited above the first and second components 100 and 104.

With reference to FIG. 8, after the third component 108 has been deposited within the center aperture 22, both the piston 14 and the inner pin 16 are again moved toward the first end 18 of the outer barrel 12 to compress the third component 108 into the first component 100 and the second component 104. This final compression forms an allograft 112 having three different components 100, 104, and 108.

The instrument 10 can be used to deposit the allograft 112 at most any location desired by a surgeon and can be used in a variety of different applications. The device advantageously provides the surgeon with control over the location of different graft components to maximize the effectiveness of the allograft 112. For example, the allograft 112 can be used to facilitate spinal fusion by using demineralized bone matrix (DBM) as the first and outer component 100, bone marrow aspirate as the second component 104, and allograft bone chips and platelet concentrate or platelet poor plasma as the third component 108. As illustrated, the DBM is pre-formed to take the shape of a cylinder having a cavity 102 and the DBM is slightly porous (FIG. 4).

With reference to FIG. 9, the allograft 112 of the configuration described above can be directed to, for example, an implant site between two broken spinal bones 150A and 150B. To implant the allograft 112 at the implantation site, the end cap 24 is removed from the outer barrel 12 and both the piston 14 and the inner pin 16 are moved to the first end 18 of the outer barrel 12 to dispense the allograft 112 from the instrument 10 in the implantation site.

The instrument 10 can also be used to form the allograft 112 with a composition that makes the allograft 112 useful for soft tissue repair, such as chin augmentation. For example, when used for soft tissue repair the first component 100 can include collagen mesh, the second component 104 can include platelet plasma concentrate, and the third component 108 can include stem cells isolated from processed lipoaspirate suspended in concentrated platelet poor plasma. This allograft 112 for soft tissue repair is implanted in the soft tissue of the patient that is in need of repair.

The instrument 10 can also be used to form the allograft 112 with a composition that makes the allograft 112 useful for nerve regeneration. For example, when used for nerve regeneration the first component 100 of the allograft 112 can include a collagen ring, the second component 104 can include platelet concentrate, and the third component 108 can include Schwann cells suspended in concentrated platelet poor plasma. The allograft 112 according to this configuration is implanted within the patient at the location where nerve regeneration is desired.

The instrument 10 can further be used to form the allograft 112 with a composition that facilitates muscle repair and regeneration. For example, when used for muscle repair or regeneration the first component 100 of the allograft 112 can include demineralized bone matrix, the second component 104 can include stem cells, and the third component 108 can include myoblast cells suspended in concentrated platelet poor plasma. The allograft 112 according to this configuration is then introduced to the area of the patient where muscle repair and/or regeneration is desired.

Still further, the instrument 10 can be used to form the allograft 112 with a composition that facilitates hair regeneration. For example, when used for hair regeneration the first component 100 can include a platelet concentrate with a thrombin calcium chloride solution and one or both of the second component 104 and the third component 108 can include adipose derived stem cells and/or follicles from an existing strip of scalp hair. The allograft 112 having this configuration is then introduced to the location on the patient where hair regeneration is desired.

The allograft 112 can be delivered to the implant site of the patient using numerous techniques known to those skilled in the art in addition to the techniques described above. Examples of additional injection techniques that can be used are provided in U.S. Pat. No. 5,585,007 titled Plasma Concentrate and Tissue Sealant Methods and Apparatuses For Making Concentrated Plasma and/or Tissue Sealant, which is incorporated herein by reference.

The use of the instrument 10 to form the allograft 112 is advantageous in that it eliminates the need to assemble the allograft 112 in vivo. The instrument 10 permits assembly of the allograft on, for example, a sterile table to provide the surgeon with more room and an increased view to assemble the allograft 112. Further, using the instrument 10 permits increased pressurization of the allograft components 100, 104, and 108 together and formation of the allograft components 100, 104, and 108 into a predetermined final graft composite geometry. Still further, use of the instrument 10 eliminates manual or digital manipulation of the allograft components 100, 104, and 108 to insure both maximum use of the available graft components 100, 104, and 108 and that the composite graft 112 is sterile. Finally, the instrument 10 provides the surgeon with control over the location of graft components. For example, if bone marrow aspirate is used it can be selectively incorporated into the surface of the composite graft where the surface cells can be more accessible at the implant site.

In addition to the embodiments described above, it must be noted that numerous alternatives and variations of the invention are also contemplated by the inventors and are within the scope of the invention. For example, one of ordinary skill in the art will recognize that the instrument can be used to manufacture allografts having only the first allograft component 100 and the second allograft component 104. Further, the instrument 10 can be used to manufacture allografts having components in addition to the first, second, and third allograft components 100, 104, and 108.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for forming a composite graft comprising:
   forming a first graft component having a first cavity;
   inserting a second graft component in the first cavity;
   compressing the second graft component and the first graft component together;
   forming a second cavity in the second graft component;
   inserting a third graft component in the second cavity, the second cavity has a predefined shape and does not collapse prior to being filled with the third graft component; and
   compressing the third graft component, the second graft component, and the first graft component together to form the composite graft;
   wherein the first graft component is inserted within an outer barrel of a graft formation instrument having an inner pin movably seated within the outer barrel.

2. The method of claim 1, wherein a piston is movably seated within the outer barrel and the inner pin is movably seated within the piston.

3. The method of claim 2, further comprising moving the inner pin into the cavity of the first graft component.

4. The method of claim 2, wherein the second graft component and the first graft component are compressed together using the piston.

5. The method of claim 2, wherein the second cavity in the second graft component is exposed by moving the inner pin and the piston distal to the first and second graft components.

6. The method of claim 2, wherein the step of compressing the third graft component, the second graft component, and the first graft component to form the composite graft is performed using both the piston and the inner pin.

7. The method of claim 1, wherein the first graft component is selected from the group consisting of demineralized bone matrix, collagen mesh, collagen ring, platelet concentrate with thrombin calcium chloride solution, and combinations thereof.

8. The method of claim 1, wherein the second graft component is selected from the group consisting of bone marrow aspirate, platelet plasma concentrate, platelet concentrate, stem cells, adipose derived stem cells, follicles from an existing strip of scalp hair, and combinations thereof.

9. The method of claim 1, wherein the third graft component is selected from the group consisting of allograft bone chips, platelet concentrate, platelet poor plasma, stem cells isolated from processed lipoaspirate suspended in concentrated platelet poor plasma, Schwann cells suspended in concentrated platelet poor plasma, myoblast cells suspended in concentrated platelet poor plasma, adipose derived stem cells, and follicles from an existing strip of scalp hair, and combinations thereof.

10. The method of claim 1, wherein the first graft component is an outer layer of the graft and the second graft component and the third graft component are both inner layers of the graft.

11. A method of forming a composite graft comprising:
forming a first graft component having a first cavity;
forming a second graft component in the first cavity of the first graft component;
forming a third graft component in a second cavity of the second graft component; and
compressing together the first graft component, the second graft component, and the third graft component with a piston;
wherein the composite graft includes an allograft.

12. The method of claim 11, wherein the composite graft is formed in a graft formation and delivery instrument.

13. The method of claim 12, further comprising using the instrument to deposit the composite graft between a first bone structure and a second bone structure to fuse the first bone structure to the second bone structure.

14. The method of claim 11, wherein the first graft component is selected from the group consisting of demineralized bone matrix, collagen mesh, collagen ring, platelet concentrate with thrombin calcium chloride solution, and combinations thereof.

15. The method of claim 11, wherein the second graft component is selected from the group consisting of bone marrow aspirate, platelet plasma concentrate, platelet concentrate, stem cells, adipose derived stem cells, follicles from an existing strip of scalp hair and combinations thereof.

16. The method of claim 11, wherein the third graft component is selected from the group consisting of allograft bone chips, platelet concentrate, platelet poor plasma, stem cells isolated from processed lipoaspirate suspended in concentrated platelet poor plasma, Schwann cells suspended in concentrated platelet poor plasma, myoblast cells suspended in concentrated platelet poor plasma, adipose derived stem cells, follicles from an existing strip of scalp hair, and combinations thereof.

17. The method of claim 11, further comprising compressing together the first graft component, the second graft component, and the third graft component with the piston and a pin that is slidably movable within the piston.

18. A method for forming a composite graft comprising:
inserting a first graft component proximate a distal end of a graft formation and delivery instrument;
positioning a pin of the instrument within a first cavity of the first graft component to define a gap between the pin and an outer wall of the first cavity;
inserting a second graft component through a valve at a sidewall of the instrument and depositing the second graft component in the gap between the pin and the outer wall;
compressing the second graft component into the first graft component using a piston of the instrument;
withdrawing the pin from within the first cavity to expose a second cavity at least partially defined by the second graft component;
inserting a third graft component through the valve and depositing the third graft component within the third cavity; and
compressing the third graft component into the first and the second graft components using the piston and the pin to form the composite graft;
wherein the second graft component has a different composition than the third graft component.

19. The method of claim 18 further comprising depositing the graft at a surgical site using the instrument.

20. The method of claim 18, wherein the first graft component is selected from the group consisting of demineralized bone matrix, collagen mesh, collagen ring, platelet concentrate with thrombin calcium chloride solution, and combinations thereof.

21. The method of claim 18, wherein the second graft component is selected from the group consisting of bone marrow aspirate, platelet plasma concentrate, platelet concentrate, stem cells, adipose derived stem cells, follicles from an existing strip of scalp hair, and combinations thereof.

22. The method of claim 18, wherein the third graft component is selected from the group consisting of allograft bone chips, platelet concentrate, platelet poor plasma, stem cells isolated from processed lipoaspirate suspended in concentrated platelet poor plasma, Schwann cells suspended in concentrated platelet poor plasma, myoblast cells suspended in concentrated platelet poor plasma, adipose derived stem cells, follicles from an existing strip of scalp hair, and combinations thereof.

23. The method of claim 18, further comprising depositing the composite graft between adjacent vertebra using the instrument to facilitate spinal fusion.

24. The method of claim 18, further comprising using the instrument to deposit the composite graft between a first bone structure and a second bone structure to fuse the first bone structure to the second bone structure.

25. A method of forming a composite graft comprising:
forming a first graft component having a first cavity;
forming a second graft component in the first cavity of the first graft component;
forming a third graft component in a second cavity of the second graft component; and
compressing together the first graft component, the second graft component, and the third graft component with a pin.

26. The method of claim 25, wherein the first graft component is selected from the group consisting of demineralized bone matrix, collagen mesh, collagen ring, platelet concentrate with thrombin calcium chloride solution, and combinations thereof.

27. The method of claim 25, wherein the second graft component is selected from the group consisting of bone marrow aspirate, platelet plasma concentrate, platelet concentrate, stem cells, adipose derived stem cells and follicles from an existing strip of scalp hair, and combinations thereof.

28. The method of claim 25, wherein the third graft component is selected from the group consisting of allograft bone chips, platelet concentrate, platelet poor plasma, stem cells isolated from processed lipoaspirate suspended in concentrated platelet poor plasma, Schwann cells suspended in concentrated platelet poor plasma, myoblast cells suspended in concentrated platelet poor plasma, and adipose derived stem cells and follicles from an existing strip of scalp hair, and combinations thereof.

29. The method of claim 25, further comprising compressing together the first graft component, the second graft component, and the third graft component with a piston, the pin is slidably movable within the piston.

30. The method of claim 25, wherein the composite graft includes an allograft.

31. The method of claim 25, wherein the composite graft includes an autograft.

32. A method of forming a composite graft comprising:
forming a first graft component having a first cavity;
forming a second graft component in the first cavity of the first graft component;
forming a third graft component in a second cavity of the second graft component; and
compressing together the first graft component, the second graft component, and the third graft component with a piston.

33. The method of claim 32, wherein the piston is slidably movable along a longitudinal axis of an elongated chamber between a first end and a second end of the chamber, the chamber having a sidewall extending between the first end and the second end;
wherein the first graft component, the second graft component, and the third graft component are positioned at the second end of the chamber; and
wherein the piston is movable to the second end to compress the first graft component, the second graft component, and the third graft component together and against the second end and the sidewall.

34. The method of claim 32, wherein the first graft component is selected from the group consisting of demineralized bone matrix, collagen mesh, collagen ring, platelet concentrate with thrombin calcium chloride solution, and combinations thereof.

35. The method of claim 32, wherein the second graft component is selected from the group consisting of bone marrow aspirate, platelet plasma concentrate, platelet concentrate, stem cells, adipose derived stem cells and follicles from an existing strip of scalp hair, and combinations thereof.

36. The method of claim 32, wherein the third graft component is selected from the group consisting of allograft bone chips, platelet concentrate, platelet poor plasma, stem cells isolated from processed lipoaspirate suspended in concentrated platelet poor plasma, Schwann cells suspended in concentrated platelet poor plasma, myoblast cells suspended in concentrated platelet poor plasma, adipose derived stem cells and follicles from an existing strip of scalp hair, and combinations thereof.

* * * * *

UNITED STATES PATENT AND TRADEMARK OFFICE
CERTIFICATE OF CORRECTION

PATENT NO. : 7,530,982 B1
APPLICATION NO. : 10/960422
DATED : May 12, 2009
INVENTOR(S) : Goshert It is certified that error appears in the above-identified patent and that said Letters Patent is hereby corrected as shown below:

Column 7
Line 2, (Claim 9) delete "and" before -- follicles --.

Column 8
Line 57, (Claim 28) delete "and" before -- adipose --.

Signed and Sealed this

Eighteenth Day of August, 2009

David J. Kappos
*Director of the United States Patent and Trademark Office*